United States Patent
Nakano et al.

(10) Patent No.: US 10,501,724 B2
(45) Date of Patent: Dec. 10, 2019

(54) METHOD FOR PRODUCING RETINAL TISSUE AND RETINA-RELATED CELLS

(71) Applicants: SUMITOMO CHEMICAL COMPANY, LIMITED, Tokyo (JP); RIKEN, Wako-shi, Saitama (JP)

(72) Inventors: Tokushige Nakano, Osaka (JP); Yoshiki Sasai, Kobe (JP); Chikafumi Ozone, Wako (JP)

(73) Assignees: SUMITOMO CHEMICAL COMPANY, LIMITED, Tokyo (JP); RIKEN, Wako (JP)

( * ) Notice: Subject to any disclaimer, the term of this patent is extended or adjusted under 35 U.S.C. 154(b) by 0 days.

(21) Appl. No.: 14/913,628

(22) PCT Filed: Aug. 22, 2014

(86) PCT No.: PCT/JP2014/072065
§ 371 (c)(1),
(2) Date: Feb. 22, 2016

(87) PCT Pub. No.: WO2015/025967
PCT Pub. Date: Feb. 26, 2015

(65) Prior Publication Data
US 2016/0251616 A1 Sep. 1, 2016

(30) Foreign Application Priority Data
Aug. 23, 2013 (JP) .................................. 2013-173285

(51) Int. Cl.
| C12N 5/079 | (2010.01) |
| A61L 27/38 | (2006.01) |
| A61K 35/30 | (2015.01) |

(52) U.S. Cl.
CPC ............ *C12N 5/0621* (2013.01); *A61K 35/30* (2013.01); *A61L 27/3804* (2013.01); *A61L 27/3834* (2013.01); *A61L 27/3895* (2013.01); *A61L 2430/16* (2013.01); *C12N 2500/33* (2013.01); *C12N 2500/44* (2013.01); *C12N 2500/90* (2013.01); *C12N 2501/155* (2013.01); *C12N 2501/19* (2013.01); *C12N 2501/385* (2013.01); *C12N 2501/415* (2013.01); *C12N 2501/727* (2013.01); *C12N 2506/02* (2013.01); *C12N 2506/45* (2013.01)

(58) Field of Classification Search
None
See application file for complete search history.

(56) References Cited

U.S. PATENT DOCUMENTS

| 7,709,605 | B2 | 5/2010 | Knopf et al. |
| 8,252,900 | B2 | 8/2012 | Knopf et al. |
| 8,956,866 | B2 | 2/2015 | Idelson et al. |
| 9,138,459 | B2 | 9/2015 | Knopf et al. |
| 9,365,830 | B2 | 6/2016 | Schulz et al. |
| 2006/0068468 | A1 | 3/2006 | Knopf et al. |
| 2009/0053809 | A1 | 2/2009 | Zander et al. |
| 2010/0105137 | A1* | 4/2010 | Takahashi ............ C12N 5/0621 435/377 |
| 2010/0267133 | A1 | 10/2010 | Knopf et al. |
| 2011/0027333 | A1* | 2/2011 | Idelson .................. A61K 35/44 424/423 |
| 2011/0274662 | A1 | 11/2011 | Malcuit et al. |
| 2013/0065299 | A1 | 3/2013 | Knopf et al. |
| 2013/0280802 | A1 | 10/2013 | Schulz et al. |
| 2014/0308743 | A1 | 10/2014 | Sasai et al. |
| 2014/0341864 | A1 | 11/2014 | Nakano et al. |
| 2015/0118749 | A1 | 4/2015 | Idelson et al. |
| 2016/0108379 | A1 | 4/2016 | Knopf et al. |
| 2016/0186136 | A1 | 6/2016 | Sasai et al. |
| 2016/0281058 | A1 | 9/2016 | Schulz et al. |

FOREIGN PATENT DOCUMENTS

| CN | 101688178 A | 3/2010 |
| CN | 103555654 A | 2/2014 |
| JP | 2008-507288 A | 3/2008 |
| JP | 2014-501518 A | 1/2014 |
| WO | WO 2006/053629 A1 | 5/2006 |
| WO | WO 2008/129554 A1 | 10/2008 |
| WO | WO 2011/043591 A2 | 4/2011 |
| WO | WO 2011/055855 A1 | 5/2011 |
| WO | WO 2013/065763 A1 | 5/2013 |
| WO | WO 2013/077425 A1 | 5/2013 |

OTHER PUBLICATIONS

Boucherie et al., "Brief Report: Self-Organizing Neuroepithelium from Human Pluripotent Stem Cells Facilitates Derivation of Photoreceptors," *Stem Cells*, 31(2): 408-414 (2013).
Eiraku et al., "Self-organizing optic-cup morphogenesis in three-dimensional culture," *Nature*, 472(7341): 51-56 (2011).
Furuta et al., "BMP4 is essential for lens induction in the mouse embryo," *Genes Dev.*, 12(23): 3764-3775 (1998).
Ikeda et al., "In vitro differentiation of telencephalic precursors and neural retinal precursors from ES cells," *Experimental Medicine*, 24(2): 188-194 and additional page of figures (2006).
Lamba et al., "Efficient generation of retinal progenitor cells from human embryonic stem cells," *Proc. Natl. Acad. Sci. USA*, 103(34): 12769-12774 (2006).

(Continued)

*Primary Examiner* — Thomas J. Visone
*Assistant Examiner* — Evelyn Y Pyla
(74) *Attorney, Agent, or Firm* — Leydig, Voit & Mayer, Ltd.

(57) ABSTRACT

The present invention provides a method for producing a retinal progenitor cell, including
(1) a first step of subjecting pluripotent stem cells to floating culture in a serum-free medium to form an aggregate of pluripotent stem cells, and
(2) a second step of subjecting the aggregate formed in step (1) to floating culture in a serum-free medium or serum-containing medium each being free of a substance acting on the Sonic hedgehog signal transduction pathway but containing a substance acting on the BMP signal transduction pathway, thereby obtaining an aggregate containing retinal progenitor cells.

15 Claims, 5 Drawing Sheets

(56) References Cited

OTHER PUBLICATIONS

Lancaster et al., "Cerebral organoids model human brain development and microcephaly," *Nature*, 501(7467): 373-379 (2013).
Lang, "Pathways regulating lens induction in the mouse," *Int. J. Dev. Biol.*, 48(8-9): 783-791 (2004).
La Torre et al., "Production and transplantation of retinal cells from human and mouse embryonic stem cells," *Retinal Development: Methods and Protocols, Methods in Molecular Biology*: 884: 229-246 (2012).
Nakano et al., "Self-Formation of Optic Cups and Storable Stratified Neural Retina from Human ESCs," *Cell Stem Cell*, 10(6): 771-785 (2012).
Osakada et al., "Control of neural differentiation from pluripotent stem cells," *Inflammation and Regeneration*, 28(3): 166-173 (2008).
Osakada et al., "Toward the generation of rod and cone photoreceptors from mouse, monkey and human embryonic stem cells," *Nat. Biotechnol.*, 26(2): 215-224 (2008).
Trousse et al., "Bmp4 Mediates Apoptotic Cell Death in the Developing Chick Eye," *J. Neurosci.*, 21(4): 1292-1301 (2001).
Watanabe et al., "Directed differentiation of telencephalic precursors from embryonic stem cells," *Nat. Neurosci.*, 8(3): 288-296 (2005).
Yang et al., "Efficient generation of lens progenitor cells and lentoid bodies from human embryonic stem cells in chemically defined conditions," *FASEB J.*, 24(9): 3274-3283 (2010).
European Patent Office, Extended European Search Report in European Patent Application No. 14838289.8 (dated Apr. 4, 2017).
Japanese Patent Office, International Search Report in International Patent Application No. PCT/JP2014/072065 (dated Nov. 25, 2014).
Japanese Patent Office, Written Opinion of the International Searching Authority in International Patent Application No. PCT/JP2014/072065 (dated Nov. 25, 2014).
Intellectual Property Office of Singapore, Search Report in Singaporean Patent Application No. 11201601294P (dated Feb. 22, 2017).
Loebel et al., "Lineage choice and differentiation in mouse embryos and embryonic stem cells," *Dev. Biol.*, 264(1): 1-14 (2003).
Meyer et al., "Modeling early retinal development with human embryonic and induced pluripotent stem cells," *Proc. Natl. Acad. Sci. U.S.A.*, 106(39): 16698-16703 (2009).
Liu, Peipei, "The distribution of BMP-4 in rat retina and optic nerve and its effects on the differentiation of oligodendrocyte precursors," *China Masters Theses Full-Text Database (Electronic Journal)*, Medicine Science Section, No. 2011/03 (2010).

* cited by examiner

METHOD FOR PRODUCING RETINAL TISSUE AND RETINA-RELATED CELLS

CROSS-REFERENCE TO RELATED APPLICATIONS

This patent application is the U.S. national phase of International Patent Application No. PCT/JP2014/072065, filed Aug. 22, 2014, which claims the benefit of Japanese Patent Application No. 2013-173285, filed on Aug. 23, 2013, which are incorporated by reference in their entireties herein.

TECHNICAL FIELD

The present invention relates to a method of producing a retinal tissue, and retina-related cells such as retinal progenitor cell and retinal layer-specific neural cell, and so on.

BACKGROUND ART

As a method of producing a three-dimensional retinal tissue from pluripotent stem cells, a method of obtaining a multi-layer retinal tissue by forming a homogeneous aggregate of pluripotent stem cells in a serum-free medium, subjecting them to floating culture in the presence of a basement membrane preparation, and to floating culture in an organ culture medium (non-patent document 1 and patent document 1), and a method of obtaining a multi-layer retinal tissue by forming a homogeneous aggregate of pluripotent stem cell in a serum-free medium containing a substance inhibiting the Wnt signal pathway, subjecting them to floating culture in the presence of a basement membrane preparation and floating culture in a serum-containing medium (non-patent document 2 and patent document 2) are shown.

DOCUMENT LIST

Patent Documents patent document 1: WO 2011/055855
patent document 2: WO 2013/077425

Non-Patent Documents non-patent document 1: Nature, 472, 51-56 (2011)
non-patent document 2: Cell Stem Cell, 10(6), 771-785 (2012)

SUMMARY OF THE INVENTION

Problems to be Solved by the Invention

The development of a production method of a retinal tissue from a pluripotent stem cell has been desired.

Means of Solving the Problems

The present invention provides a method of producing a retinal tissue, and retina-related cells such as retinal progenitor cell and retinal layer-specific neural cell from pluripotent stem cells, and so on.

Accordingly, the present invention provides:

[1] a method for producing a retinal progenitor cell, comprising
(1) a first step of subjecting pluripotent stem cells to floating culture in a serum-free medium to form an aggregate of pluripotent stem cells, and
(2) a second step of subjecting the aggregate formed in step (1) to floating culture in a serum-free medium or serum-containing medium each being free of a substance acting on the Sonic hedgehog signal transduction pathway and containing a substance acting on the BMP signal transduction pathway, thereby obtaining an aggregate containing retinal progenitor cells (hereinafter sometimes to be indicated as production method 1 of the present invention);

[2] a method for producing a retinal tissue, comprising
(1) a first step of subjecting pluripotent stem cells to floating culture in a serum-free medium to form an aggregate of pluripotent stem cells,
(2) a second step of subjecting the aggregate formed in step (1) to floating culture in a serum-free medium or serum-containing medium each being free of a substance acting on the Sonic hedgehog signal transduction pathway and containing a substance acting on the BMP signal transduction pathway, thereby obtaining an aggregate containing retinal progenitor cells, and
(3) a third step of subjecting the aggregate formed in step (2) to floating culture in a serum-free medium or serum-containing medium each being free of any of a substance acting on the Sonic hedgehog signal transduction pathway, a substance acting on the BMP signal transduction pathway and a substance acting on the Wnt signal pathway, thereby obtaining an aggregate containing retinal tissues and being substantially free of non-neural head ectoderm (hereinafter sometimes to be indicated as production method 2 of the present invention);

[3] a method for producing a retinal layer-specific neural cell, comprising
(1) a first step of subjecting pluripotent stem cells to floating culture in a serum-free medium to form an aggregate of pluripotent stem cells,
(2) a second step of subjecting the aggregate formed in step (1) to floating culture in a serum-free medium or serum-containing medium each being free of a substance acting on the Sonic hedgehog signal transduction pathway and containing a substance acting on the BMP signal transduction pathway, thereby obtaining an aggregate containing retinal progenitor cells, and
(3) a third step of subjecting the aggregate formed in step (2) to floating culture in a serum-free medium or serum-containing medium each being free of any of a substance acting on the Sonic hedgehog signal transduction pathway, a substance acting on the BMP signal transduction pathway and a substance acting on the Wnt signal pathway until the intended retinal layer-specific neural cells appear, thereby obtaining an aggregate containing retinal tissues containing the intended retinal layer-specific neural cells and being substantially free of non-neural head ectoderm (hereinafter sometimes to be indicated as production method 3 of the present invention);

[4] the method of any of the aforementioned [1] to [3], wherein the pluripotent stem cells are primate pluripotent stem cells;

[5] the method of any of the aforementioned [1] to [4], wherein the pluripotent stem cells are human pluripotent stem cells;

[6] the method of any of the aforementioned [1] to [5], wherein the step (1) and step (2) are performed in the presence of a serum replacement;

[7] the method of any of the aforementioned [1] to [6], wherein the floating culture is performed in the absence of a basement membrane preparation;

[8] the method of any of the aforementioned [1] to [7], wherein the substance acting on the BMP signal transduction pathway is one or more proteins selected from the group consisting of BMP2, BMP4, BMP7 and GDF7;

[9] the method of any of the aforementioned [1] to [8], wherein the substance acting on the BMP signal transduction pathway is added to the medium between day 1 and day 15 from the start of the floating culture in step (1);

[10] a reagent for evaluating toxicity or drug efficacy, comprising a retinal progenitor cell, retinal tissue or retinal layer-specific neural cell, the cell or tissue being produced by the method of any of the aforementioned [1] to [9];

[11] a method of evaluating toxicity or drug efficacy of a test substance, comprising bringing a retinal progenitor cell, retinal tissue or retinal layer-specific neural cell, the cell or tissue being produced by the method of any of the aforementioned [1] to [9], into contact with the test substance, and examining the influence of the substance on the cell or tissue;

[12] a therapeutic agent for a disease due to a disorder of a retinal tissue, comprising a retinal progenitor cell, a retinal tissue or a retinal layer-specific neural cell, the cell or tissue being produced by the method of any of the aforementioned [1] to [9];

[13] a method of treating a disease due to a disorder of a retinal tissue, comprising transplanting an effective amount of a retinal progenitor cell, a retinal tissue or a retinal layer-specific neural cell, the cell or tissue being produced by the method of any of the aforementioned [1] to [9], to a subject in need of the transplantation;

[14] a retinal progenitor cell, a retinal tissue or a retinal layer-specific neural cell, the cell or tissue being produced by the method of any of the aforementioned [1] to [9], for use in the treatment of a disease due to a disorder of a retinal tissue;

and so on.

Effect of the Invention

According to the production method of the present invention, a retinal progenitor cell, a retinal tissue or a retinal layer-specific neural cell can be produced with high efficiency. In the production method of the present invention, since a retinal progenitor cell, a retinal tissue or a retinal layer-specific neural cell can be obtained by floating culture of an aggregate without adding a basement membrane preparation to a medium, namely, in the absence of a basement membrane preparation, the risk of contamination of the obtained cell or tissue with a component derived from a heterologous species is reduced. According to the production method of the present invention, a retinal tissue, or retina-related cells such as retinal progenitor cell and retinal layer-specific neural cell can be efficiently provided for the purpose of toxicity or efficacy evaluation of a chemical substance etc., a transplantation treatment and so on.

DESCRIPTION OF EMBODIMENTS

Figure 1:
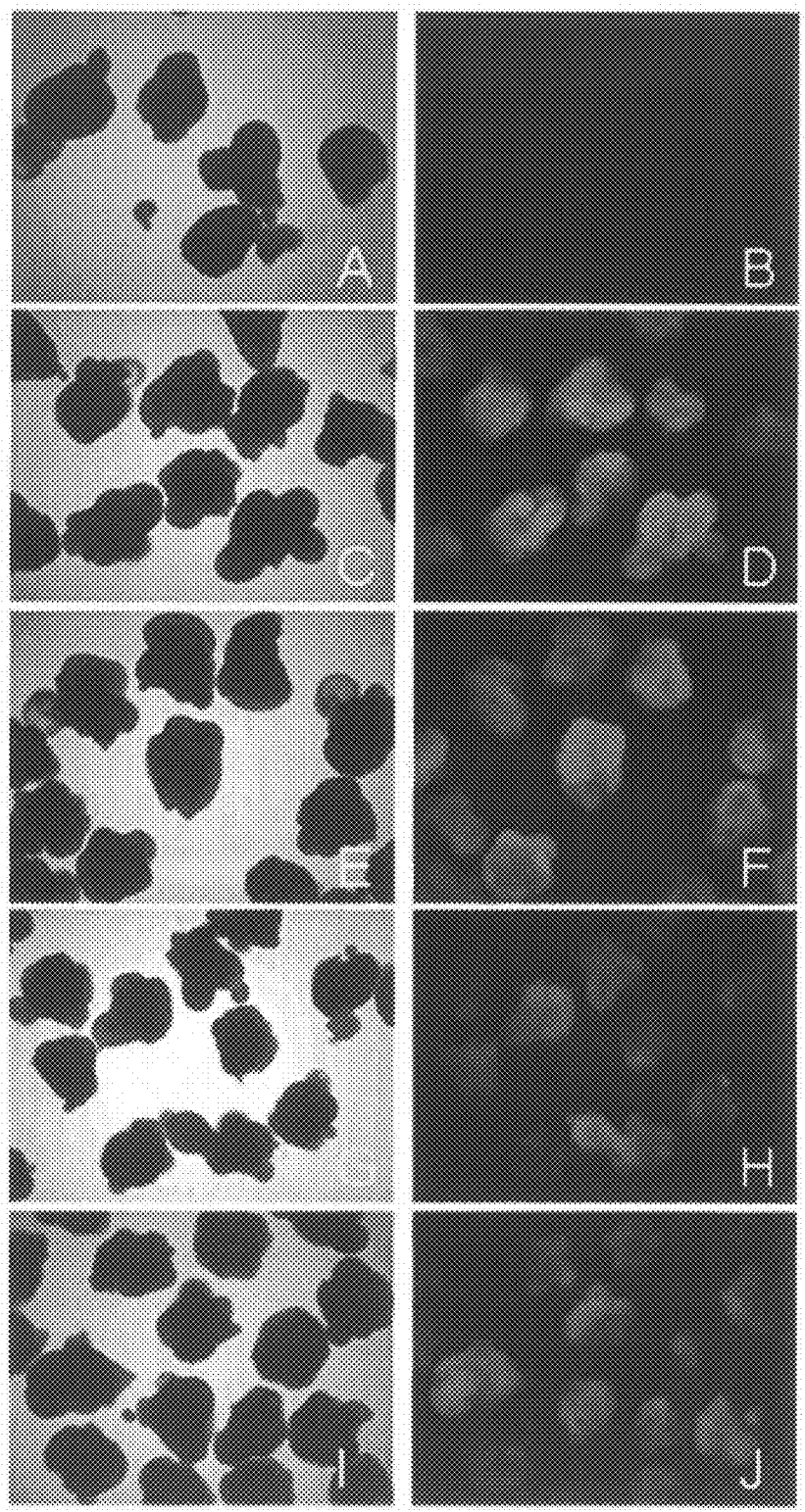
FIG. 1 shows light field image (A) and fluorescence image (B) at day 18 from the start of floating culture of aggregates, derived from RAX::GFP knock-in human embryonic stem cells, without adding a substance acting on the BMP signal transduction pathway to the medium, light field image (C) and fluorescence image (D) at day 18 from the start of floating culture of aggregates, derived from RAX::GFP knock-in human embryonic stem cells, in a medium supplemented with BMP2 to 100 ng/ml at day 3 from the start of the floating culture, light field image (E) and fluorescence image (F) at day 18 from the start of floating culture of aggregates, derived from RAX::GFP knock-in human embryonic stem cells, in a medium supplemented with BMP4 at 1.5 nM at day 3 from the start of the floating culture, light field image (G) and fluorescence image (H) at day 18 from the start of floating culture of aggregates, derived from RAX::GFP knock-in human embryonic stem cells, in a medium supplemented with BMP7 at 100 ng/ml at day 3 from the start of the floating culture, and light field image (I) and fluorescence image (J) at day 18 from the start of floating culture of aggregates, derived from dRAX::GFP knock-in human embryonic stem cells, in a medium supplemented with GDF7 at 100 ng/ml at day 3 from the start of the floating culture.

Mode(s) for carrying out the present invention is explained in detail below.

The "vector" in the present invention means a vector capable of transferring a desired polynucleotide sequence into an intended cell. Examples of such vector include a vector capable of autonomously replicating in a host cell such as prokaryotic cell, yeast, animal cell, plant cell, insect cell, animal individual and plant individual, a vector capable of being incorporated into a chromosome of a host cell, a vector containing a promoter at a position suitable for polynucleotide transcription, and so on.

Of such vectors, a vector suitable for cloning is sometimes indicated as a "cloning vector". Examples of the cloning vector include a vector generally having multiple cloning sites containing a plurality of restriction enzyme sites. For example, the vectors described in "Molecular Cloning (3rd edition)" by Sambrook, J and Russell, D. W., Appendix 3 (Volume 3), Vectors and Bacterial strains. A3.2 (Cold Spring Harbor USA, 2001)) can be mentioned.

The "vector" in the present invention also includes "expression vector" and "reporter vector". In the "expression vector", various regulatory elements in addition to a structural gene and a promoter that regulates the expression thereof may be linked in such a manner that they can be operable in the host cell. In the "reporter vector", various regulatory elements in addition to a reporter gene and a promoter that regulates the expression thereof may be linked in such a manner that they can be operable in the host cell. Examples of the "regulatory element" include terminator and enhancer. The "expression vector" and "reporter vector" may further include selection marker genes such as drug resistance gene.

Examples of the "cloning vector" include (a) lambda FIX vector, which is a phage vector, for the construction of a genomic library, (b) lambda ZAP vector, which is a phage vector, for the construction of a cDNA library, and (c) plasmid vectors such as pBluescript II SK+/−, pGEM, and pCR2.1 vector, for cloning of genomic DNA. Examples of the "expression vector" include plasmid vectors such as pSV2/neo vector, pcDNA vector, pUC18 vector, pUC19 vector, pRc/RSV vector, pLenti6/V5-Dest vector, pAd/CMV/V5-DEST vector, pDON-AI-2/neo vector, and pMEI-5/neo vector. Examples of the "reporter vector" include pGL2 vector, pGL3 vector, pGL4.10 vector, pGL4.11 vector, pGL4.12 vector, pGL4.70 vector, pGL4.71 vector, pGL4.72 vector, pSLG vector, pSLO vector, pSLR vector, pEGFP vector, pAcGFP vector, and pDsRed vector. These vectors can be utilized as appropriate by reference to the aforementioned Molecular Cloning reference.

As a technique for introducing a nucleic acid molecule into a cell, for example, transformation, transduction, transfection and so on can be mentioned. As such introduction technique, for example, the methods described in Ausubel F. A. et al. ed. (1988), Current Protocols in Molecular Biology, Wiley, New York, N.Y.; Sambrook J. et al. (1987), Molecular Cloning: A Laboratory Manual, 2nd Ed. and 3rd Ed.; Cold Spring to Harbor Laboratory Press, Cold Spring Harbor, N.Y.; Sambrook J. et al. (2001) Molecular Cloning: A Laboratory Manual, 3rd Ed., Cold Spring Harbor Laboratory Press, Cold Spring Harbor, N.Y.; extra issue, Experimental Medicine "transgene & expression analysis experiment method" YODOSHA CO., LTD., 1997, and so on can be specifically mentioned. As the technique for confirming intracellular introduction of a gene, for example, Northern blot analysis or Western blot analysis can be mentioned.

The "floating culture" in the present invention means cultivating under conditions prohibiting adhesion of cell or cell mass to a cell culture vessel material etc.

The cell culture vessel to be used in floating culture is not particularly limited as long as it enables "floating culture", and those of ordinary skill in the art can appropriately determine same. Examples of such cell culture vessel include flask, tissue culture flask, dish, petri dish, tissue culture dish, multidish, microplate, microwell plate, micropore, multiplate, multiwell plate, chamber slide, schale, tube, tray, culture bag, and roller bottle. Since these cell culture vessels are used for floating culture, they are preferably cell non-adhesive. As a cell non-adhesive vessel, one having its, surface not artificially treated to improve cell adhesiveness (e.g., coating treatment with extracellular matrix, etc.) and so on can be used.

The medium to be generally used in the present invention can be prepared from a medium used for culture of animal cell as a basal medium. Examples of the basal medium include those that can be used for culturing animal cells, such as BME medium, BGJb medium, CMRL1066 medium, Glasgow MEM medium, Improved MEM Zinc Option medium, IMDM medium, Medium199 medium, Eagle MEM medium, αMEM medium, DMEM medium, F-12 medium, Ham's medium, RPMI1640 medium, Fischer's medium, and mixed medium thereof.

The "serum-free medium" in the present invention means a medium free of unadjusted or unpurified serum. In the present invention, a medium containing purified blood-derived components and animal tissue-derived components (e.g., growth factor) is considered to be a serum-free medium unless unadjusted or unpurified serum is contained therein.

The serum-free medium may contain a serum replacement. Examples of the serum replacement include those appropriately containing, for example, albumin, transferrin, fatty acid, collagen precursor, trace element, 2-mercaptoethanol or 3' thiolglycerol, an equivalent thereof and so on. Such serum replacement can be prepared by, for example, the method described in WO98/30679. In addition, the serum replacement can be a commercially available product. Examples of such commercially available serum replacement include KNOCKOUT™ Serum Replacement (manufactured by Invitrogen: hereinafter sometimes to be also indicated as KSR), Chemically defined lipid concentrate (manufactured by Gibco), and GLUTAMAX' supplement (manufactured by Gibco).

The serum-free medium to be used for floating culture may contain fatty acid or lipid, amino acid (e.g., non-essential amino acid), vitamin, growth factor, cytokine, antioxidant, 2-mercaptoethanol, pyruvic acid, buffering agent, inorganic salts and so on.

To avoid complicated preparation, a serum-free medium supplemented with an appropriate amount (e.g., about 1-about 20%) of commercially available KSR can be used as the serum-free medium (e.g., medium obtained by adding 10% KSR and 450 μM 1-monothioglycerol to a 1:1 mixture of F-12 medium and IMDM medium).

The "serum-containing medium" in the present invention means a medium containing unadjusted or unpurified serum. The medium may contain fatty acid or lipid, amino acid (e.g., non-essential amino acid), vitamin, growth factor, cytokine, antioxidant, 2-mercaptoethanol, 1-monothioglycerol, pyruvic acid, buffering agent, inorganic salts and so on.

The "basement membrane preparation" in the present invention refers to one containing basement membrane-constituting components having a function to control cell form, differentiation, growth, motility, expression of function and so on which are similar to those of epithelial cell, when intended cells capable of forming a basement membrane are plated thereon and cultured. Here, the "basement membrane constituting component" refers to an extracellular matrix molecule in the form of a thin membrane present between epithelial cell layer and interstitial cell layer and so on in animal tissues. A basement membrane preparation can be produced by, for example, removing cells capable of forming a basement membrane, which adhere onto a support via a basement membrane, with a solution capable of dissolving the lipid of the cells, an alkali solution and so on. Examples of preferable basement membrane preparation include products commercially available as basement membrane components (e.g., MATRIGEL™ extracellular matrix (manufactured by Beckton Dickinson)), and extracellular matrix molecules known as basement membrane components (e.g., laminin, type IV collagen, heparan sulfate proteoglycan, entactin and so on).

MATRIGEL™ extracellular matrix is a product extracted from a basement membrane derived from Engelbreth Holm Swam (EHS) mouse sarcoma. The main component of MATRIGEL™ extracellular matrix is type IV collagen, laminin, heparan sulfate proteoglycan, and entactin. In addition to these, TGF-0, fibroblast growth factor (FGF), tissue plasminogen activator, and a growth factor naturally produced by EHS tumor are contained. The "growth factor reduced product" of MATRIGEL' extracellular matrix has a lower growth factor concentration than common MATRIGEL™ extracellular matrix, and the standard concentration thereof is <0.5 ng/ml for EGF, <0.2 ng/ml for NGF, <5 pg/ml for PDGF, 5 ng/ml for IGF-1, and 1.7 ng/ml for TGF-β.

The "medium containing substance X" in the present invention means a medium supplemented with an exogeneous substance X or a medium containing an exogenous substance X, and the "medium free of substance X" means a medium not supplemented with an exogenous substance X or a medium not containing an exogenous substance X. Here, the "exogenous substance X" means a substance X exogeneous to a cell or tissue to be cultured in the medium, and an endogenous substance X produced by the cell or tissue is not included therein.

For example, a "medium containing a substance acting on the BMP signal transduction pathway" is a medium supplemented with an exogenous substance acting on the BMP signal transduction pathway or a medium containing an exogenous substance acting on the BMP signal transduction pathway. A "medium free of a substance acting on the Sonic hedgehog signal transduction pathway" is a medium not supplemented with an exogenous substance acting on the Sonic hedgehog signal transduction pathway or a medium not containing an exogenous substance acting on the Sonic hedgehog signal transduction pathway.

The "primates" in the present invention mean mammals belonging to primate. Examples of the primates include Strepsirrhini such as lemur, loris, and Tsubai, and Haplorhini such as monkey, anthropoid ape, and human.

In the present invention, the "stem cell" refers to a cell that maintains the same differentiation capacity even after cell division, which can contribute to the regeneration of a tissue thereof when the tissue is injured. Here, the stem cell may be an embryonic stem cell (hereinafter sometimes to be referred to as ES cell) or a tissue stem cell (also called tissular stem cell, tissue-specific stem cell or somatic stem cell), or an artificial pluripotent stem cell (iPS cell: induced pluripotent stem cell). As is appreciated from the fact that the above-mentioned stem cell-derived tissue cell can regenerate a tissue, it is known that the stem cell can differentiate into a normal cell close to one in a living body.

Stem cells are available from given organizations, or a commercially available product can also be purchased. For example, human embryonic stem cells, KhES-1, KhES-2 and KhES-3, are available from Kyoto University's Institute for Frontier Medical Sciences. EB5 cell is available from RIKEN, and D3 cell line is available from ATCC, each of which is a mouse embryonic stem cell.

Stem cells can be maintained by culturing according to a method known per se. For example, human stem cells can be maintained by culturing in a medium supplemented with KNOCKOUT™ Serum Replacement (Invitrogen). Mouse stem cells can be maintained by adding fetal calf serum (FCS) and Leukemia Inhibitory Factor (LIF) and culturing without feeder cells.

In the present invention, the "pluripotent stem cell" refers to a stem cell that can be cultured in vitro and has an ability to differentiate into any cell (triploblast (ectoderm, mesoderm, endoderm)-derived tissue) constituting a living body except for placenta (pluripotency), and an embryonic stem cell (ES cell) is included in the pluripotent stem cell. The "pluripotent stem cell" is obtained from fertilized egg, clone embryo, reproductive stem cell, and stem cell in a tissue. A cell having artificial differentiation pluripotency similar to that of embryonic stem cells, after introducing several kinds of genes into a somatic cell (also called artificial pluripotent stem cell) is also included in the pluripotent stem cell. Pluripotent stem cell can be produced by a method known per se. Examples of the production method include the methods described in Cell, 2007, 131(5) pp. 861-872 and Cell, 2006, 126(4) pp. 663-676.

In the present invention, the "embryonic stem cell (ES cell)" refers to a stem cell having a self replication ability and multipotency (particularly, "pluripotency"), which is a pluripotent stem cell derived from an early embryo. Embryonic stem cell was first established in 1981, and has also been applied to the generation of knockout mouse since 1989. In 1998, a human embryonic stem cell was established, which is also being utilized for regenerative medicine.

In the present invention, the "artificial pluripotent stem cell" refers to a cell induced to have multipotency by directly reprogramming a differentiated cell such as fibroblast etc. by the expression of several kinds of genes such as Oct3/4, Sox2, Klf4, and Myc, which was established by Yamanaka et al. in mouse cell in 2006 (Cell. 2006, 126(4), pp. 663-676). In 2007, induced pluripotent stem cell was also established in human fibroblast, and has multipotency similar to that of embryonic stem cells (Cell, 2007, 131(5) pp. 861-872; Science, 2007, 318(5858) pp. 1917-1920; Nat. Biotechnol., 2008, 26(1) pp. 101-106).

A genetically-modified pluripotent stem cell can be produced, for example, using a homologous recombination technique. Examples of the gene on the chromosome to be modified include a cell marker gene, a histocompatibility antigen gene, a gene related to a disease due to a disorder of nerve system cell and so on. A target gene on the chromosome can be modified by the methods described in Manipulating the Mouse Embryo, A Laboratory Manual, Second Edition, Cold Spring Harbor Laboratory Press (1994); Gene Targeting, A Practical Approach, IRL Press at Oxford University Press (1993); Bio Manual series 8, gene targeting, Production of mutant mouse by using ES cells, YODOSHA CO., LTD. (1995) and so on.

To be specific, for example, the genomic gene of a target gene to be modified (e.g., cell marker gene, histocompatibility antigen gene, disease-related gene and so on) is isolated, and a target vector used for homologous recombination of the target gene is produced using the isolated genomic gene. The produced target vector is introduced into stem cells, and cells showing homologous recombination between the target gene and the target vector are selected, whereby stem cells having modified gene on the chromosome can be produced.

As a method for isolating the genomic gene of the target gene, known methods described in Molecular Cloning, A Laboratory Manual, Second Edition, Cold Spring Harbor Laboratory Press (1989), Current Protocols in Molecular Biology, John Wiley & Sons (1987-1997) and so on can be mentioned. Moreover, the genomic gene of the target gene can be isolated using genomic DNA library screening system (manufactured by Genome Systems), Universal GenomeWalker Kits (manufactured by CLONTECH) and so on.

A target vector used for homologous recombination of the target gene can be produced, and a homologous recombinant can be efficiently selected according to the methods described in Gene Targeting, A Practical Approach, IRL Press at Oxford University Press (1993); Bio Manual series 8, gene targeting, Production of mutant mouse by using ES cells, YODOSHA CO., LTD. (1995) and so on. The target vector may be any of replacement type and insertion type, and the selection method may be positive selection, promoter selection, negative selection, polyA selection and so on.

As a method for selecting an intended homologous recombinant from the selected cell lines, Southern hybridization method, PCR method and so on for genomic DNA can be mentioned.

The "aggregate" in the present invention refers to a mass of the cells dispersed in the medium but gathered to form same. The "aggregate" in the present invention includes an aggregate formed by the cells dispersed at the start of the floating culture and an aggregate already formed at the start of the floating culture.

When cells are gathered to form cell aggregates and the aggregates are subjected to floating culture, to "form aggregate" means to "rapidly aggregate a given number of dispersed cells" to form qualitatively homogeneous cell aggregates.

In the present invention, it is preferable to rapidly gather pluripotent stem cells to allow for formation of an aggregate of pluripotent stem cells. By forming an aggregate of pluripotent stem cells in this manner, an epithelium-like structure can be formed with good reproducibility in the cells induced to differentiate from the formed aggregate.

Examples of the experimental operation to form an aggregate include a method involving keeping cells in a small space by using a plate with small wells (96 well plate), micropore and so on, a method involving aggregating cells by centrifugation for a short time using a small centrifugation tube.

Whether aggregates of pluripotent stem cells have been formed and whether an epithelial-like structure has been formed in the cells forming the aggregate can be determined based on the size and cell number of aggregates, macroscopic morphology, microscopic morphology by tissue staining analysis and uniformity thereof, expression of differentiation and undifferentiation markers and uniformity thereof, control of expression of differentiation marker and synchronism thereof, reproducibility of differentiation efficiency between aggregates, and so on.

In the present invention, the "tissue" refers to a structure of a cell population, which has a conformation wherein more than one type of cell different in the shape and property are sterically configured in a given pattern.

In the present invention, the "retinal tissue" means a retinal tissue wherein at least two or more types of cells such as photoreceptors, horizontal cells, bipolar cells, amacrin cells, retinal ganglion cells, their precursor cells or retinal progenitor cells thereof, which constitute respective retinal layers in living retina, are sterically arranged in layers. With regard to each cell, which cell constitutes which retinal layer can be confirmed by a known method, for example, the presence or absence or the level of the expression of a cell marker and the like.

The "retinal layer" in the present invention means each layer constituting the retina. Specific examples thereof include retinal pigment epithelial layer, photoreceptor layer, external limiting membrane, outer nuclear layer, outer plexiform layer, inner nuclear layer, inner plexiform layer, ganglion cell layer, nerve fiber layer and inner limiting membrane.

The "retinal layer-specific neural cell" in the present invention means a neural cell constituting a retinal layer and specific to the retinal layer. Examples of the retinal layer-specific neural cell include bipolar cell, ganglion cell, amacrine cell, horizontal cell, photoreceptor, pigment epithelium cell, rod cell and cone cell.

The "retinal progenitor cell" in the present invention refers to a progenitor cell that can be differentiated into any mature retinal cell of a photoreceptor, a horizontal cell, a bipolar cell, an amacrine cell, a retinal ganglion cell and a retinal pigment epithelial cell.

The photoreceptor precursor cell, horizontal precursor cell, bipolar precursor cell, amacrine precursor cell, retinal ganglion precursor cell and retinal pigment epithelial precursor cell are precursor cells determined to differentiate into a photoreceptor, a horizontal cell, a bipolar cell, an amacrine cell, a retinal ganglion cell, and a retinal pigment epithelial cell, respectively.

Examples of the retinal cell marker include Rax and PAX6 expressed in retinal progenitor cells, Nkx2.1 expressed in progenitor cells of hypothalamus neuron but not expressed in retinal progenitor cells, Sox1 expressed in hypothalamus neuroepithelium and not expressed in retina, Crx expressed in precursor cells of photoreceptor and the like. Examples of the retinal layer-specific neural cell marker include Chx10 and L7 expressed in bipolar cells, Tuj1 and Brn3 expressed in ganglion cells, Calretinin expressed in amacrine cells, Calbindin expressed in horizontal cells, Rhodopsin and Recoverin expressed in photoreceptors, RPE65 and Mitf expressed in pigment epithelium cells, Nrl expressed in rod cells, Rxr-gamma expressed in cone cells and the like.

The production method 1 of the present invention is a method for producing retinal progenitor cells, which includes the following steps (1) and (2):

(1) a first step of subjecting pluripotent stem cells to floating culture in a serum-free medium to form an aggregate of pluripotent stem cells, and (2) a second step of subjecting the aggregate formed in step (1) to floating culture in a serum-free medium or serum-containing medium each being free of a substance acting on the Sonic hedgehog signal transduction pathway and containing a substance acting on the BMP signal transduction pathway, thereby obtaining an aggregate containing retinal progenitor cells.

Step (1) for subjecting pluripotent stem cells to floating culture in a serum-free medium to form an aggregate of pluripotent stem cells is explained.

The serum-free medium used in step (1) is not particularly limited as long as it is as mentioned above. For example, a serum-free medium not supplemented with any of a substance acting on the BMP signal transduction pathway and a substance inhibiting the Wnt signal pathway can be used. To avoid complicated formulation process, a serum-free medium supplemented with an appropriate amount of a serum replacement such as commercially available KSR (e.g., a medium obtained by adding 10% KSR, 450 µM 1-monothioglycerol and 1× Chemically Defined Lipid Concentrate to a 1:1 mixture of IMDM and F-12) is preferably used. The amount of KSR to be added to a serum-free medium is generally about 1% to about 20%, preferably about 2% to about 20%, in the case of, for example, human ES cells.

The culture conditions such as culture temperature, $CO_2$ concentration in step (1) can be appropriately determined. The culture temperature is, for example, about 30° C. to about 40° C., preferably about 37° C. The $CO_2$ concentration is, for example, about 1 to about 10%, preferably about 5%.

The concentration of the pluripotent stem cells in step (1) can be determined as appropriate to form aggregates of pluripotent stem cells more uniformly and efficiently. For example, when human ES cells are subjected to floating culture using a 96 well microwell plate, a liquid prepared to about $1 \times 10^3$ to about $5 \times 10^5$ cells, preferably about $3 \times 10^3$ to about $5 \times 10^4$ cells, more preferably about $5 \times 10^3$ to about $3 \times 10^4$ cells, most preferably about $1.2 \times 10^4$ cells, per well is added to a well, and the plate is left standing to form aggregates.

The time of floating culture necessary for forming aggregates can be determined as appropriate according to the pluripotent stem cell to be used, to allow for uniform aggregation of the cells. To form uniform aggregates, it is desirably as short as possible. For example, in the case of human ES cells, aggregates are formed preferably within about 24 hr, more preferably within about 12 hr. The time for aggregate formation can be appropriately adjusted by controlling the tools for aggregating the cells, centrifugation conditions and so on.

Whether aggregates of pluripotent stem cells have been formed can be determined based on the size and cell number of aggregates, macroscopic morphology, microscopic morphology by tissue staining analysis and uniformity thereof, expression of differentiation and undifferentiation markers and uniformity thereof, control of expression of differentiation marker and synchronism thereof, reproducibility of differentiation efficiency between aggregates, and so on.

Step (2) including subjecting the aggregate formed in step (1) to floating culture in a serum-free medium or serum-containing medium each being free of a substance acting on the Sonic hedgehog signal transduction pathway and containing a substance acting on the BMP signal transduction pathway, thereby obtaining an aggregate containing retinal progenitor cells is explained.

As the medium to be used in step (2), for example, a serum-free medium or a serum-containing medium not supplemented with a substance acting on the Sonic hedgehog signal transduction pathway and supplemented with a substance acting on the BMP signal transduction pathway is used, and addition of a basement membrane preparation is not necessary.

The serum-free medium or serum-containing medium to be used as such medium is not particularly limited as long as it is as mentioned above. To avoid complicated formulation process, a serum-free medium supplemented with an appropriate amount of a serum replacement such as commercially available KSR (e.g., a medium obtained by adding 10% KSR, 450 µM 1-monothioglycerol and 1× Chemically Defined Lipid Concentrate to a 1:1 mixture of IMDM and F-12) is preferably used. The amount of KSR to be added to a serum-free medium is generally about 1% to about 20%, preferably about 2% to about 20%, in the case of, for example, human ES cells.

As the serum-free medium to be used in step (2), the serum-free medium used in step (1) may be used as it is as long as it does not contain a substance acting on the Sonic hedgehog signal transduction pathway, or may be replaced with a fresh serum-free medium. When the serum-free medium used in step (1), which does not contain a BMP signal transduction pathway substance, is directly used for step (2), a substance acting on the BMP signal transduction pathway only needs to be added to the medium.

A substance acting on the Sonic hedgehog (hereinafter sometimes to be indicated as Shh) signal transduction pathway is a substance that can enhance signal transduction mediated by Shh. Examples of the substance acting on the Shh signal transduction pathway include proteins belonging to the Hedgehog family (e.g., Shh), Shh receptor, Shh receptor agonist, Purmorphamine, SAG and so on.

A medium free of "a substance acting on the Sonic hedgehog signal transduction pathway" also includes a medium substantially free of a substance acting on the Sonic hedgehog signal transduction pathway, such as a medium free of a substance acting on the Sonic hedgehog signal transduction pathway, at a concentration exerting an adverse influence on the selective differentiation into retinal progenitor cell and retinal tissue.

A substance acting on the BMP signal transduction pathway is a substance that can enhance signal transduction pathway mediated by BMP. Examples of the substance acting on the BMP signal transduction pathway include BMP proteins such as BMP2, BMP4 or BMP7, GDF proteins such as GDF7, anti-BMP receptor antibody, BMP partial peptide and so on. BMP2 protein, BMP4 protein and BMP7 protein are available from, for example, R&D Systems, and GDF7 protein is available from, for example, Wako Pure Chemical Industries, Ltd.

The concentration of a substance acting on the BMP signal transduction pathway only needs to be a concentration capable of inducing differentiation of cells forming pluripotent stem cell aggregates into retinal cells. In the case of BMP4, for example, it is added to a medium at a concentration of about 0.01 nM to about 1 μM, preferably about 0.1 nM to about 100 nM, more preferably about 1.5 nM.

A substance acting on the BMP signal transduction pathway only needs to be added after about 24 hours from the start of the floating culture in step (1), and may be added to the medium within several days from the start of the floating culture (e.g., within 15 days). Preferably, a substance acting on the BMP signal transduction pathway is added to the medium between day 1 and day 15, more preferably between day 1 and day 9, most preferably at day 3, from the start of the floating culture.

After a substance acting on the BMP signal transduction pathway is added to the medium and differentiation induction of cells forming pluripotent stem cell aggregates into retinal cells is started, the substance acting on the BMP signal transduction pathway does not need to be added to the medium, and the medium can be exchanged with a serum-free medium or serum-containing medium each being free of a substance acting on the BMP signal transduction pathway, whereby the cost of the medium can be suppressed. A cell in which differentiation induction into a retinal cell has been started can be confirmed, for example, by detecting the expression of Rax gene in the cell. It is also possible to confirm the time when the differentiation induction into retinal cell was started by subjecting the aggregates formed in step (1) by using a pluripotent stem cell, in which a fluorescence reporter protein gene such as GFP has been knocked-in in the Rax gene locus, to floating culture in the presence of a substance acting on the BMP signal transduction pathway at a concentration necessary for differentiation induction into retinal cells, and detecting the fluorescence emitted from the expressed fluorescence reporter protein. One of the embodiments of step (2) is a step including subjecting the aggregates formed in step (1) to floating culture in a serum-free medium or serum-containing medium each containing a substance acting on the BMP signal transduction pathway at a concentration necessary for differentiation induction into retinal cells and being free of a substance acting on the Sonic hedgehog signal transduction pathway until a cell expressing the Rax gene appears to obtain an aggregate containing a retinal progenitor cell.

The culture conditions such as culture temperature, $CO_2$ concentration in step (2) can be appropriately determined. The culture temperature is, for example, about 30 to about 40° C., preferably about 37° C. The $CO_2$ concentration is, for example, about 1 to about 10%, preferably about 5%.

That an aggregate containing a retinal progenitor cell has been obtained can be confirmed by, for example, detecting that the aggregate contains a cell expressing Rax or PAX6, which is a retinal progenitor cell marker.

The obtained aggregate containing a retinal progenitor cell may be used as it is as a reagent for evaluating toxicity or drug efficacy. It is also possible to obtain a highly pure retinal progenitor cell by subjecting the aggregate containing a retinal progenitor cell to a dispersion treatment (e.g., trypsin/EDTA treatment), and selecting the obtained cells by using FACS.

The production method 2 of the present invention is a method for producing a retinal tissue, comprising the following steps (1), (2) and (3):
(1) a first step of subjecting pluripotent stem cells to floating culture in a serum-free medium to form an aggregate of pluripotent stem cells,
(2) a second step of subjecting the aggregate formed in step (1) to floating culture in a serum-free medium or serum-containing medium each being free of a substance acting on the Sonic hedgehog signal transduction pathway and containing a substance acting on the BMP signal transduction pathway, thereby obtaining an aggregate containing retinal progenitor cells, and
(3) a third step of subjecting the aggregate formed in step (2) to floating culture in a serum-free medium or serum-containing medium each being free of any of a substance acting on the Sonic hedgehog signal transduction pathway, a substance acting on the BMP signal transduction pathway and a substance acting on the Wnt signal pathway, thereby obtaining an aggregate containing retinal tissues and being substantially free of non-neural head ectoderm.

The step (1) and step (2) of the production method 2 of the present invention can be performed similarly to step (1) and step (2) of the production method 1 of the present invention.

The step (3) including subjecting the aggregate formed in step (2) to floating culture in a serum-free medium or serum-containing medium each being free of any of a substance acting on the Sonic hedgehog signal transduction pathway, a substance acting on the BMP signal transduction pathway and a substance acting on the Wnt signal pathway, thereby obtaining an aggregate containing retinal tissues and being substantially free of non-neural head ectoderm is explained.

The medium used in step (3) is, for example, a serum-free medium or serum-containing medium not supplemented with any of a substance acting on the Sonic hedgehog signal transduction pathway, a substance acting on the BMP signal transduction pathway and a substance acting on the Wnt signal pathway.

The medium "free of any of a substance acting on the Sonic hedgehog signal transduction pathway, a substance acting on the BMP signal transduction pathway and a substance acting on the Wnt signal pathway" also includes a medium substantially free of any of a substance acting on the Sonic hedgehog signal transduction pathway, a substance acting on the BMP signal transduction pathway and a substance acting on the Wnt signal pathway, for example, a medium not containing any of a substance acting on the Sonic hedgehog signal transduction pathway, a substance acting on the BMP signal transduction pathway and a substance acting on the Wnt signal pathway, at a concentration exerting an adverse influence on the selective differentiation into retinal tissues.

The medium "not supplemented with any of a substance acting on the Sonic hedgehog signal transduction pathway, a substance acting on the BMP signal transduction pathway and a substance acting on the Wnt signal pathway" also includes a medium substantially not supplemented with any of a substance acting on the Sonic hedgehog signal transduction pathway, a substance acting on the BMP signal transduction pathway and a substance acting on the Wnt signal pathway, for example, a medium not supplemented with any of a substance acting on the Sonic hedgehog signal transduction pathway, a substance acting on the BMP signal transduction pathway and a substance acting on the Wnt signal pathway, at a concentration exerting an adverse influence on the selective differentiation into retinal tissues.

The serum-free medium or serum-containing medium to be used as such medium is not particularly limited as long as it is as mentioned above. To avoid complicated formulation process, for example, a serum-free medium supplemented with an appropriate amount of a serum replacement such as commercially available KSR (e.g., a medium obtained by adding 10% KSR, 450 µM 1-monothioglycerol and 1× Chemically Defined Lipid Concentrate to a 1:1 mixture of IMDM and F-12) is preferably used. The amount of KSR to be added to a serum-free medium is generally about 1% to about 20%, preferably about 2% to about 20%, in the case of, for example, human ES cells.

The substance acting on the Wnt signal pathway is a substance that can enhance signal transduction mediated by Wnt. Examples of the substance acting on the Wnt signal pathway include protein belonging to Wnt family (e.g., Wnt1, Wnt3a, Wnt7a), Wnt receptor, Wnt receptor agonist, GSK3β inhibitor (e.g., 6-Bromoindirubin-3'-oxime (BIO), CHIR99021, Kenpaullone) and so on.

The culture conditions such as culture temperature, $CO_2$ concentration, $O_2$ concentration in step (3) can be appropriately determined. The culture temperature is, for example, about 30° C. to about 40° C., preferably about 37° C. The $CO_2$ concentration is, for example, about 1 to about 10%, preferably about 5%. The $O_2$ concentration is not less than about 18%, for example, about 20% to about 70%, preferably about 20% to about 60%, more preferably about 20% to about 50%.

While the culture period in step (3) is not particularly limited, it is generally 48 hr or longer, preferably 7 days or longer.

In the aggregates subjected to floating culture in such manner, the retinal tissue is present to cover the surface of the aggregate. The retinal tissue can be confirmed by, after completion of the floating culture, fixing the aggregates with a fixative such as para-formaldehyde solution, preparing a frozen section, and confirming formation of a retinal tissue having a layer structure by an immunostaining method and so on. Since respective layers of a retinal tissue are composed of different retinal progenitor cells (photoreceptor, horizontal cell, bipolar cell, amacrine cell, retinal ganglion cell), formation of a layer structure can be confirmed by an immunostaining method using antibodies against the markers expressed in these cells.

It is also possible to physically cut out the retinal tissue present on the surface of aggregates with tweezers and so on. In this case, since a neural tissue other than a retinal tissue may be formed on the surface of each aggregate, a part of the neural tissue cut out from the aggregate is severed and confirmed by the immunostaining method as described below and so on, whereby the tissue is confirmed to be a retinal tissue.

In an aggregate containing the retinal tissue and substantially free of non-neural head ectoderm, for example, RAX positive tissues are observed in the immunostained images of the aggregate cryosection, and RAX negative tissues are not observed in the outside thereof.

Retinal tissues can be obtained highly efficiently from human pluripotent stem cells by the production method 2 of the present invention. Since the retinal tissues obtained by the production method 2 of the present invention contain a neuron specific to each of the retina layers, it is also possible to obtain a cell constituting retinal tissues such as photoreceptor, horizontal cell, bipolar cell, amacrine cell, ganglion cell, or progenitor cells of these and the like. What cell was available from the obtained retinal tissue can be confirmed by a method known per se, for example, expression of a cell marker.

An aggregate containing the obtained retinal tissue and substantially free of non-neural head ectoderm may be used as it is as a reagent for evaluating toxicity or drug efficacy. It is also possible to obtain a highly pure retinal tissue constituting cell by subjecting the aggregate containing a retinal tissue and substantially free of non-neural head ectoderm to a dispersion treatment (e.g., trypsin/EDTA treatment), and selecting the obtained cells by using FACS.

The production method 3 of the present invention is a method for producing a retinal layer-specific neural cell, comprising the following steps (1), (2) and (3):

(1) a first step of subjecting pluripotent stem cells to floating culture in a serum-free medium to form an aggregate of pluripotent stem cells, (2) a second step of subjecting the aggregate formed in step (1) to floating culture in a serum-free medium or serum-containing medium each being free of a substance acting on the Sonic hedgehog signal transduction pathway and containing a substance acting on the BMP signal transduction pathway, thereby obtaining an aggregate containing retinal progenitor cells, and (3) a third step of subjecting the aggregate formed in step (2) to floating culture in a serum-free medium or serum-containing medium each being free of any of a substance acting on the Sonic hedgehog signal transduction pathway, a substance acting on the BMP signal transduction pathway and a substance acting on the Wnt signal pathway until the intended retinal layer-specific neural cells appear, thereby obtaining an aggregate containing retinal tissues containing the intended retinal layer-specific neural cells and being substantially free of non-neural head ectoderm.

The step (1) and step (2) of the production method 3 of the present invention can be performed similarly to step (1) and step (2) of the production method 1 of the present invention.

The step (3) including subjecting the aggregate formed in step (2) to floating culture in a serum-free medium or serum-containing medium each being free of any of a substance acting on the Sonic hedgehog signal transduction pathway, a substance acting on the BMP signal transduction pathway and a substance acting on the Wnt signal pathway until the intended retinal layer-specific neural cells appear, thereby obtaining an aggregate containing retinal tissues containing the intended retinal layer-specific neural cells and being substantially free of non-neural head ectoderm is explained.

The medium used in step (3) is, for example, a serum-free medium or serum-containing medium not supplemented with any of a substance acting on the Sonic hedgehog signal transduction pathway, a substance acting on the BMP signal transduction pathway and a substance acting on the Wnt signal pathway.

The medium "free of any of a substance acting on the Sonic hedgehog signal transduction pathway, a substance acting on the BMP signal transduction pathway and a substance acting on the Wnt signal pathway" also includes a medium substantially free of any of a substance acting on the Sonic hedgehog signal transduction pathway, a substance acting on the BMP signal transduction pathway and a substance acting on the Wnt signal pathway, for example, a medium not containing any of a substance acting on the Sonic hedgehog signal transduction pathway, a substance acting on the BMP signal transduction pathway and a substance acting on the Wnt signal pathway, at a concentration exerting an adverse influence on the selective differentiation into retinal tissues and retinal layer-specific neural cells.

The medium "not supplemented with any of a substance acting on the Sonic hedgehog signal transduction pathway, a substance acting on the BMP signal transduction pathway and a substance acting on the Wnt signal pathway" also includes a medium substantially not supplemented with any of a substance acting on the Sonic hedgehog signal transduction pathway, a substance acting on the BMP signal transduction pathway and a substance acting on the Wnt signal pathway, for example, a medium not supplemented with any of a substance acting on the Sonic hedgehog signal transduction pathway, a substance acting on the BMP signal transduction pathway and a substance acting on the Wnt signal pathway, at a concentration exerting an adverse influence on the selective differentiation into retinal tissues and retinal layer-specific neural cells.

The serum-free medium or serum-containing medium to be used as such medium is not particularly limited as long as it is as mentioned above. For example, a serum-containing medium obtained by adding 10% fetal calf serum, N2 supplement, 100 μM taurine, and 500 nM retinoic acid to DMEM-F12 medium, a serum-free medium supplemented with an appropriate amount of a serum replacement such as commercially available KSR (e.g., a medium obtained by adding 10% KSR, 450 μM 1-monothioglycerol and 1× Chemically Defined Lipid Concentrate to a 1:1 mixture of IMDM and F-12) and the like can be mentioned.

The culture conditions such as culture temperature, $CO_2$ concentration, $O_2$ concentration in step (3) can be appropriately determined. The culture temperature is, for example, about 30° C. to about 40° C., preferably about 37° C. The $CO_2$ concentration is, for example, about 1% to about 10%, preferably about 5%. The $O_2$ concentration is not less than about 18%, for example, about 20% to about 70%, preferably about 20% to about 60%, more preferably about 20% to about 50%.

The culture period in step (3) varies depending on the intended retinal layer-specific neural cell and is, for example, about 7 days to about 200 days.

In the aggregate subjected to floating culture in such manner, the retinal tissue containing the retinal layer-specific neural cell is present to cover the surface of the aggregate. The retinal tissue can be confirmed by, after completion of the floating culture, fixing the aggregates with a fixative such as para-formaldehyde solution, preparing a frozen section, and confirming formation of a retinal tissue having a layer structure by an immunostaining method and so on. Since respective layers of a retinal tissue are composed of different retinal progenitor cells (photoreceptor, horizontal cell, bipolar cell, amacrine cell, retinal ganglion cell), formation of a layer structure can be confirmed by an immunostaining method using antibodies against the markers expressed in these cells.

In an aggregate containing the retinal tissue containing a retinal layer-specific neural cell and substantially free of non-neural head ectoderm, for example, RAX positive tissues are observed in the immunostained images of the aggregate cryosection, and RAX negative tissues are not observed in the outside thereof.

Since the retinal tissues obtained by the production method 3 of the present invention contain a neuron specific to each of the retina layers, it is also possible to obtain a retinal layer-specific neural cell such as photoreceptor, horizontal cell, bipolar cell, amacrine cell and ganglion cell. What cell was available from the obtained retinal tissue can be confirmed by a method known per se, for example, expression of a cell marker.

An aggregate containing the obtained retinal tissue to containing retinal layer-specific neural cell and substantially free of non-neural head ectoderm may be used as it is as a reagent for evaluating toxicity or drug efficacy. It is also possible to obtain a highly pure retinal layer-specific neural cell by subjecting the aggregate containing a retinal tissue containing retinal layer-specific neural cell and substantially free of non-neural head ectoderm to a dispersion treatment (e.g., trypsin/EDTA treatment), and selecting the obtained cells by using FACS.

The obtained retinal layer-specific neural cells can be directly cultured furthermore, or subjected to a dispersion treatment (e.g., trypsin/EDTA treatment) and further culture under adhesion conditions. In the case of adhesion culture, a cell adhesive culture vessel, for example, a culture vessel after a coating treatment with an extracellular matrix etc. (e.g., poly-D-lysine, laminin, fibronectin), is preferably used. The culture conditions of the adhesion culture such as culture temperature, $CO_2$ concentration, and $O_2$ concentration can be determined as appropriate. In this case, culture may be performed in the presence of a known differentiation induction substance and a neurotrophic factor. Examples of the differentiation induction substance and neurotrophic factor include NGF (Biochem. Biophys. Res. Commun., 199, 552 (1994)), retinoic acid (Dev. Biol., 168, 342 (1995); J. Neurosci., 16, 1056 (1996)), BMP inhibitory factor (Nature, 376, 333-336 (1995)), IGF (Genes&Development, 15, 3023-8 (2003)), BDNF, NT3, NT4 and so on.

The produced retinal tissues and retinal layer-specific neural cells can be confirmed using the presence or absence of expression of a cell marker and the like as indices, or by combining them as necessary. The obtained retinal layer-specific neural cell can also be identified by the observation of the cell morphology. A desired, particular cell can also be isolated based on such marker expression pattern and cell morphology.

The retinal progenitor cell, retinal tissue or retinal layer-specific neural cell produced by the production methods 1 to 3 of the present invention can also be used for screening for a therapeutic drug for a disease due to a disorder of retinal tissue or retina-related cell, or a transplantation material for cell treatment, a material for the study of diseases or a drug discovery material for a therapeutic drug for a cell damage due to other etiology. In addition, they can be utilized for the study, test and so on of such toxicity as phototoxicity in the toxicity and drug efficacy evaluation of chemical substances and so on.

Examples of the disease due to a disorder of retinal tissue or retina-related cell include organic mercury poisoning, chloroquine retinopathy, retinitis pigmentosa, age-related macular degeneration, glaucoma, diabetic retinopathy, neonatal retinopathy, and so on.

The retinal progenitor cell, retinal tissue or retinal layer-specific neural cell produced by the production methods 1 to 3 the present invention can be used as retina for transplantation, which is used for supplementing a damaged cell or disordered tissue itself in a cell damage state (e.g., used for transplantation operation) and so on.

EXAMPLES

The present invention is explained in more detail in the following by referring to Examples, which are not to be construed as limitative.

Example 1: Production Example of Aggregate Containing Retinal Progenitor Cells RAX::GFP knock-in human ES cells (KhES-1-derived; Cell Stem Cell, 2012, 10(6) 771-785) were cultured according to the methods described in "Ueno, M. et al. PNAS 2006, 103(25), 9554-9559" and "Watanabe, K. et al. Nat Biotech 2007, 25, 681-686". As the medium, a medium obtained by adding 20% KSR (KNOCKOUT™ Serum Replacement; Invitrogen), 0.1 mM 2-mercaptoethanol, 2 mM L-glutamine, 1× non-essential amino acid, 5 ng/ml bFGF to DMEM/F12 medium (Sigma) was used. The cultured ES cells were dispersed into single cells by using TrypLE Express (Invitrogen), and the singly dispersed ES cells were suspended in 100 μl of a serum-free medium at $1.2 \times 10^4$ cells per one well of a non-cell adhesive 96 well culture plate (sumilon spheroid plates, SUMITOMO BAKELITE Co., Ltd.) and subjected to floating culture at 37° C., 5% $CO_2$. As the serum-free medium therefor, a serum-free medium obtained by adding 10% KSR, 450 μM 1-monothioglycerol, 1× Chemically defined lipid concentrate, 20 μM Y27632 to a 1:1 mixture of F-12 medium and IMDM medium was used. At day 3 from the start of the floating culture, any of human recombinant BMP4 (R&D) (final concentration 1.5 nM), BMP2 (R&D) (final concentration 100 ng/ml), BMP7 (R&D) (final concentration 100 ng/ml) and GDF7 (R&D) (final concentration 100 ng/ml) was added and floating culture was performed. Similar culture was also performed under conditions free of the addition of any of the substances acting on the BMP signal transduction pathway. A half amount of the culture medium in the well was exchanged every 3 days with the above-mentioned medium not supplemented with any of substance acting on the BMP signal transduction pathway. At day 18 from the start of the floating culture, fluorescence microscopic observation was performed. When cultured under conditions without addition of a substance acting on the BMP signal transduction pathway, GFP expressing cells indicating induction of retinal progenitor cells were scarcely observed (FIG. 1A, B). In contrast, GFP expressing cells clearly increased under culture conditions including addition of any of BMP2 (FIG. 1C, D), BMP4 (FIG. 1E, F), BMP7 (FIG. 1G, H), and GDF7 (FIG. 1I, J).

Example 2: Production Example of Retinal Tissue—1

RAX::GFP knock-in human ES cells (KhES-1-derived; Cell Stem Cell, 2012, 10(6) 771-785) were cultured according to the methods described in "Ueno, M. et al. PNAS 2006, 103(25), 9554-9559" and "Watanabe, K. et al. Nat Biotech 2007, 25, 681-686". As the medium, a medium obtained by adding 20% KSR (KNOCKOUT™ Serum Replacement; Invitrogen), 0.1 mM 2-mercaptoethanol, 2 mM L-glutamine, 1× non-essential amino acid, 5 ng/ml bFGF to DMEM/F12 medium (Sigma) was used. The cultured ES cells were dispersed into single cells by using TrypLE Express (Invitrogen), and the singly dispersed ES cells were suspended in 100 μl of a serum-free medium at $1.2 \times 10^4$ cells per one well of a non-cell adhesive 96 well culture plate (sumilon spheroid plates, SUMITOMO BAKELITE Co., Ltd.) and subjected to floating culture at 37° C., 5% $CO_2$. As the serum-free medium therefor, a serum-free medium obtained by adding 10% KSR, 450 μM 1-monothioglycerol, 1× Chemically defined lipid concentrate, 20 μM Y27632 to a 1:1 mixture of F-12 medium and IMDM medium was used. Human recombinant BMP4 (R&D) (final concentration 1.5 nM) was added at any time point from simultaneously with the start of the floating culture, day 1 from the start of the floating culture, day 2 from the start of the floating culture, and day 3 from the start of the floating culture, and floating culture was performed. Similar culture was also performed under conditions free of the addition of a substance acting on the BMP signal transduction pathway. A half amount of the culture medium in the well was exchanged every 3 days with the above-mentioned medium not supplemented with a substance acting on the BMP signal transduction pathway. At day 18 from the start of the floating culture, aggregates were transferred from the 96 well plate to a floating culture dish, and floating culture was continuously performed in a serum-free medium obtained by adding 10% KSR, 450 μM 1-monothioglycerol, 1× Chemically defined lipid concentrate to a 1:1 mixture of F-12 medium and IMDM medium. At day 26 from the start of the floating culture, fluorescence microscopic observation and measurement of the GFP positive cells by FACS were conducted.

Figure 2:
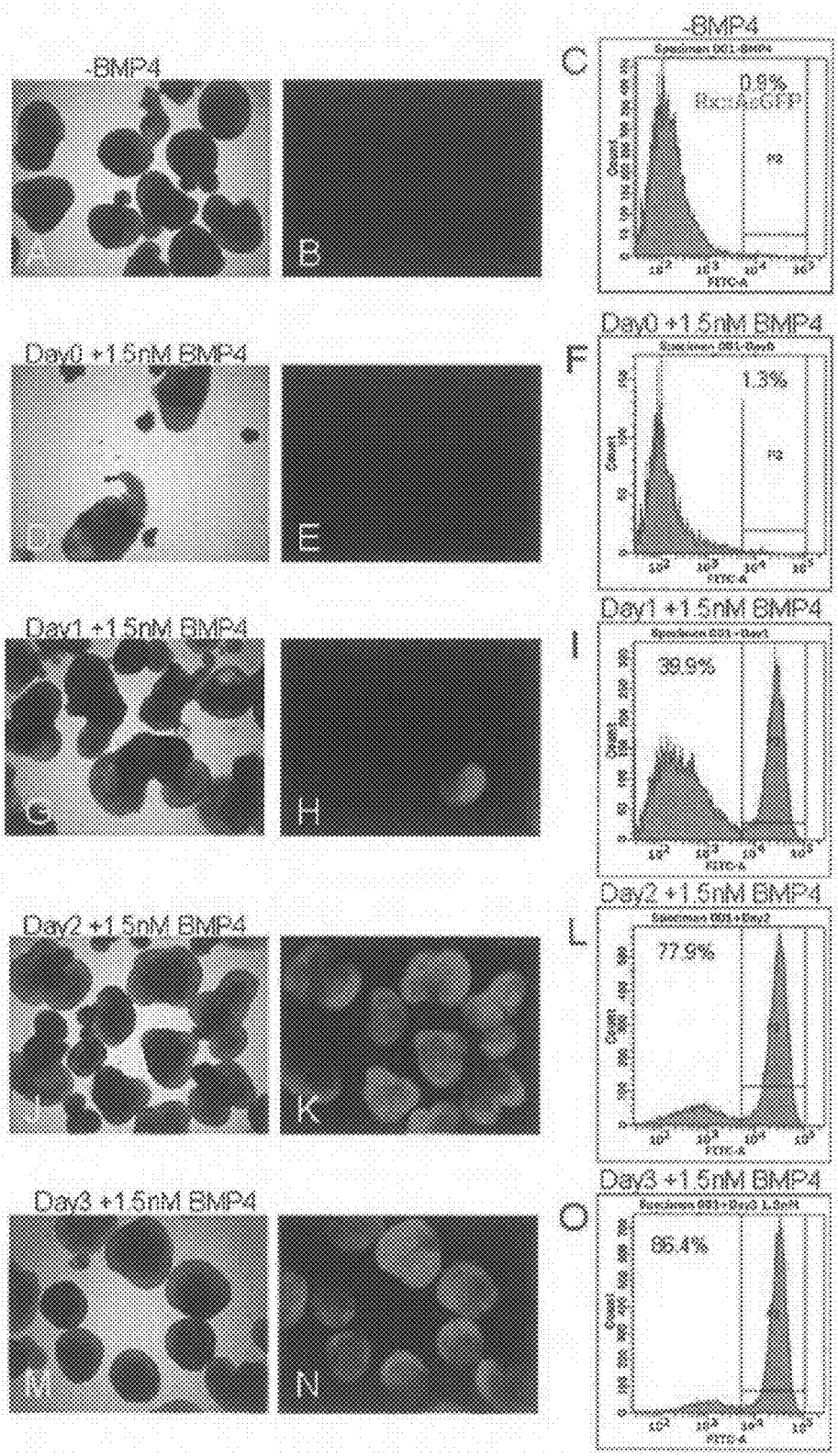
FIG. 2 shows light field image (A), fluorescence image (B) and FACS histogram (C) at day 26 from the start of floating culture of aggregates, derived from RAX::GFP knock-in human embryonic stem cells, without adding a substance acting on the BMP signal transduction pathway to the medium, light field image (D) and fluorescence image (E) and FACS histogram (F) at day 26 from the start of floating culture of aggregates, derived from RAX::GFP knock-in human embryonic stem cells, in a medium supplemented with BMP4 to 1.5 nM simultaneously with the start of the floating culture (day 0), light field image (G), fluorescence image (H) and FACS histogram (I) at day 26 from the start of floating culture of aggregates, derived from RAX::GFP knock-in human embryonic stem cells, in a medium supplemented with BMP4 to 1.5 nM at day 1 from the start of the floating culture, light field image (J), fluorescence image (K) and FACS histogram (L) at day 26 from the start of floating culture of aggregates, derived from RAX::GFP knock-in human embryonic stem cells, in a medium supplemented with BMP4 to 1.5 nM at day 2 from the start of the floating culture, and light field image (M), fluorescence image (N) and FACS histogram (O) at day 26 from the start of floating culture of aggregates, derived from RAX::GFP knock-in human embryonic stem cells, in a medium supplemented with BMP4 at 1.5 nM at day 3 from the start of the floating culture.

GFP expressing cell indicating induction of retinal progenitor cells was not found under conditions without addition of a substance acting on the BMP signal transduction pathway (FIG. 2A, B, C) and under conditions with the addition of BMP4 simultaneously with the start of the floating culture (FIG. 2D, E, F). In contrast, GFP expressing cell clearly increased under conditions with the addition of BMP4 at any time point from day 1 from the start of the floating culture (FIG. 2G, H, I), day 2 from the start of the floating culture (FIG. 2J, K, L), and day 3 from the start of the floating culture (FIG. 2M, N, O). In all conditions, RAX::GFP negative tissue was not observed on the outside of the RAX::GFP positive tissue formed. According to the measurement results by FACS, not less than 85% of the cells were GFP positive under conditions with the addition of BMP4 at day 3 from the start of the floating culture (FIG. 2O). The above results reveal that addition of a substance acting on the BMP signal transduction pathway at day 1 or later, preferably at day 3, from the start of the floating culture is effective for the production of an aggregate containing retinal tissue and substantially free of non-neural head ectoderm.

Example 3: Production Example of Retinal Tissue—2

RAX::GFP knock-in human ES cells (KhES-1-derived; Cell Stem Cell, 2012, 10(6) 771-785) were cultured according to the methods described in "Ueno, M. et al. PNAS 2006, 103(25), 9554-9559" and "Watanabe, K. et al. Nat Biotech 2007, 25, 681-686". As the medium, a medium obtained by adding 20% KSR (KNOCKOUT™ Serum Replacement; Invitrogen), 0.1 mM 2-mercaptoethanol, 2 mM L-glutamine, 1× non-essential amino acid, 5 ng/ml bFGF to DMEM/F12 medium (Sigma) was used. The cultured ES cells were dispersed into single cells by using TrypLE Express (Invitrogen), and the singly dispersed ES cells were suspended in 100 μl of a serum-free medium at $1.2 \times 10^4$ cells per one well of a non-cell adhesive 96 well culture plate (sumilon spheroid plates, SUMITOMO BAKELITE Co., Ltd.) and subjected to floating culture at 37° C., 5% $CO_2$. As the serum-free medium therefor, a serum-free medium obtained by adding 10% KSR, 450 µM 1-monothioglycerol, 1× Chemically defined lipid concentrate, 20 µM Y27632 to a 1:1 mixture of F-12 medium and IMDM medium was used. Human recombinant BMP4 (R&D) (final concentration 1.5 nM) was added at any time point from day 6 from the start of the floating culture, day 9 from the start of the floating culture, day 12 from the start of the floating culture and day 15 from the start of the floating culture, and floating culture was performed. Similar culture was also performed under conditions free of the addition of a substance acting on the BMP signal transduction pathway. A half amount of the culture medium in the well was exchanged every 3 days with the above-mentioned medium not supplemented with a substance acting on the BMP signal transduction pathway. At day 18 from the start of the floating culture, aggregates were transferred from the 96 well plate to a floating culture dish, and floating culture was continuously performed in a serum-free medium obtained by adding 10% KSR, 450 µM 1-monothioglycerol, 1× Chemically defined lipid concentrate to a 1:1 mixture of F-12 medium and IMDM medium. At day 24 from the start of the floating culture, fluorescence microscopic observation was conducted.

Figure 3:
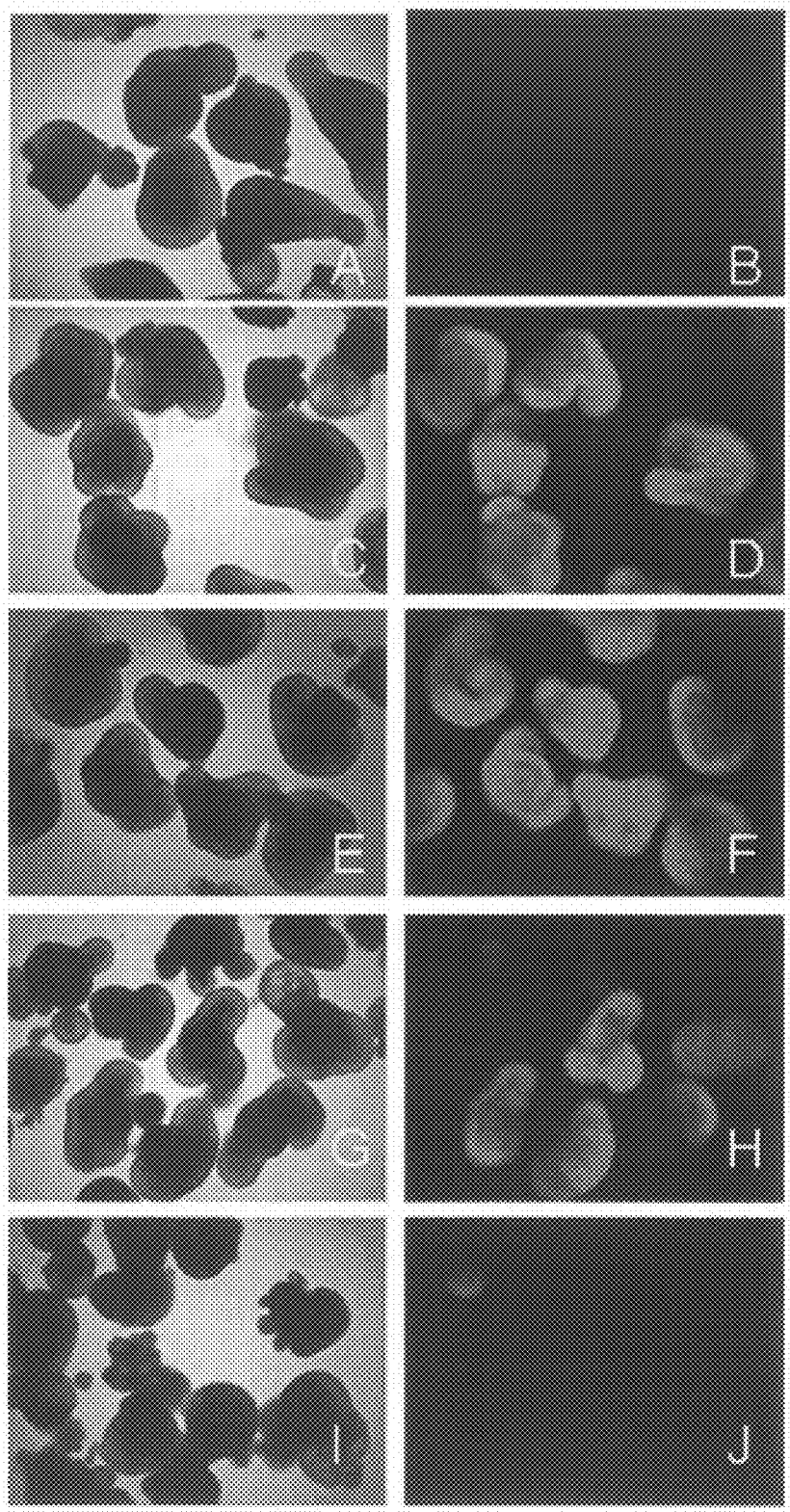
FIG. 3 shows light field image (A) and fluorescence image (B) at day 24 from the start of floating culture of aggregates, derived from RAX::GFP knock-in human embryonic stem cells, without adding a substance acting on the BMP4 signal transduction pathway to the medium, light field image (C) and fluorescence image (D) at day 24 from the start of floating culture of aggregates, derived from RAX::GFP knock-in human embryonic stem cells, in a medium supplemented with BMP4 to 1.5 nM at day 6 from the start of the floating culture, light field image (E) and fluorescence image (F) at day 24 from the start of floating culture of aggregates, derived from RAX::GFP knock-in human embryonic stem cells, in a medium supplemented with BMP4 at 1.5 nM at day 9 from the start of the floating culture, light field image (G) and fluorescence image (H) at day 24 from the start of floating culture of aggregates, derived from RAX::GFP knock-in human, embryonic stem cells, in a medium supplemented with BMP4 at 1.5 nM at day 12 from the start of the floating culture, and light field image (I) and fluorescence image (J) at day 24 from the start of floating culture of aggregates, derived from dRAX::GFP knock-in human embryonic stem cells, in a medium supplemented with BMP4 at 1.5 nM at day 15 from the start of the floating culture.

As a result, GFP expressing cell indicating induction of retinal progenitor cells was not found under conditions without addition of a substance acting on the BMP signal transduction pathway (FIG. 3A, B). In contrast, GFP expressing cell clearly increased under conditions with the addition of BMP4 at any time point from day 6 from the start of the floating culture (FIG. 3C, D), day 9 from the start of the floating culture (FIG. 3E, F), and day 12 from the start of the floating culture (FIG. 3G, H). Under conditions with the addition of BMP4 at day 15 from the start of the floating culture, GFP expressing cells were induced but the efficiency was low (FIG. 3I, J). In all conditions, RAX::GFP negative tissue was not observed on the outside of the RAX::GFP positive tissue formed. The above results reveal that addition of a substance acting on the BMP signal transduction pathway on or before day 15 from the start of the floating culture is effective for the production of an aggregate containing retinal tissue and substantially free of non-neural head ectoderm.

Example 4: Production Example of Retinal Tissue—3

At day 18 from the start of the floating culture, the aggregates containing GFP expressing cell, which were obtained in Example 1, were transferred from the 96 well plate to a floating culture dish, and floating culture was continuously performed in a serum-free medium obtained by adding 10% KSR, 450 µM 1-monothioglycerol, 1× Chemically defined lipid concentrate to a 1:1 mixture of F-12 medium and IMDM medium. At day 26 from the start of the floating culture, the aggregates were fixed with 4% para-formaldehyde solution, cryosection was prepared, and the tissue structure was confirmed by the immunostaining method.

Figure 4:
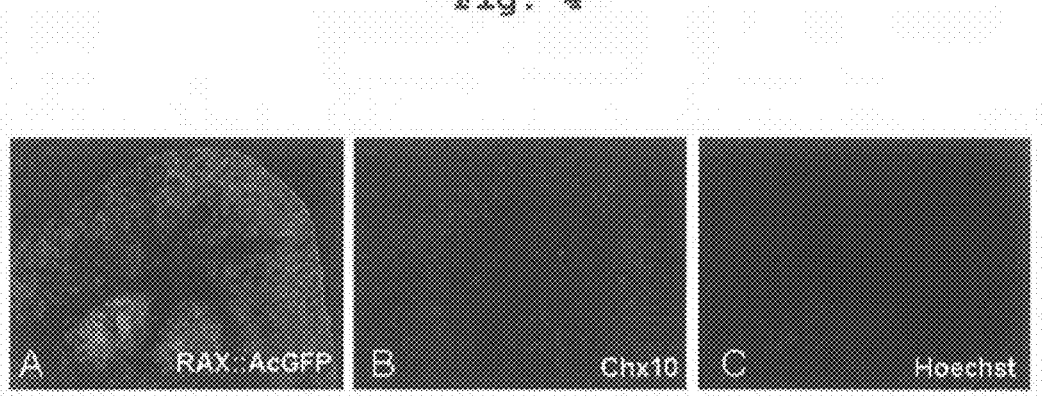
FIG. 4 shows GFP fluorescence image (A), fluorescence immunostained image (B) using an anti-Chx10 antibody and Hoechst stained image (C) of cryosections of aggregates, derived from RAX::GFP knock-in human embryonic stem cells, which were subjected to floating culture up to day 26 from the start of the floating culture in a medium supplemented with BMP4 at 1.5 nM at day 3 from the start of the floating culture.

At day 26 from the start of the floating culture, all layers were RAX::GFP positive, and the outer layer was positive to Chx10, which is a retina stem cell marker (FIG. 4A, B, C). No tissue such as nonneural ectoderm was present on the outside of the RAX::GFP positive epithelium. It was shown that the production method of the present invention can produce retinal tissue highly efficiently from human ES cells.

Example 5: Production Example of Retinal Layer-Specific Neural Cell

Figure 5:
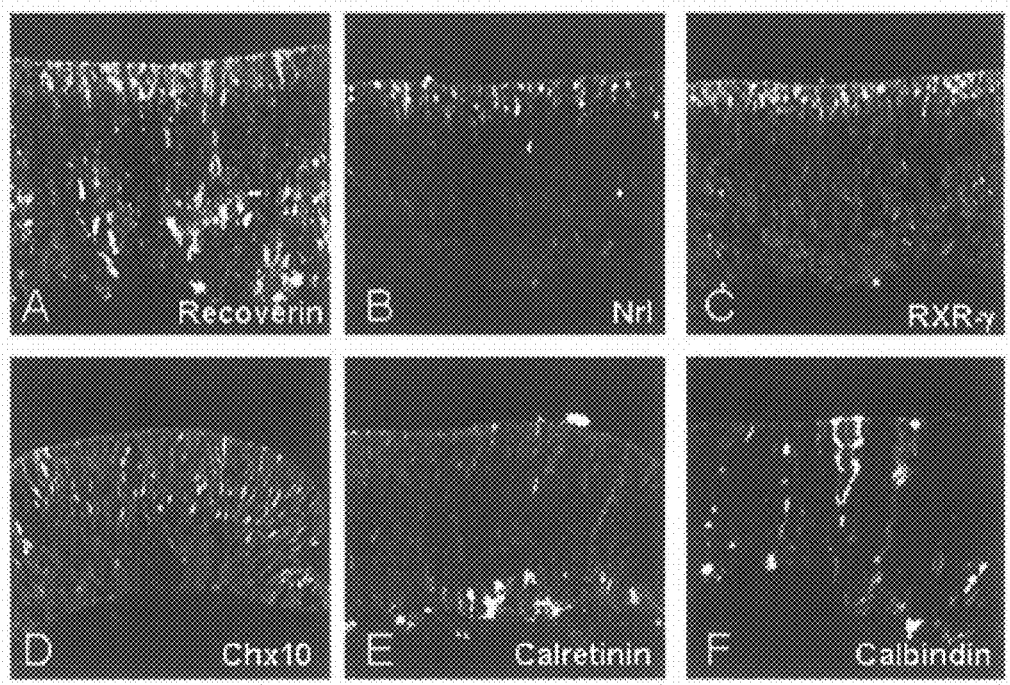
FIG. 5 shows immunostained image (A) using an anti-Recoverin antibody, immunostained image (B) using an anti-Nrl antibody, immunostained image (C) using an anti-RXR-gamma antibody, immunostained image (D) using an anti-Chx10 antibody, immunostained image (E) using an anti-Calretinin antibody, and immunostained image (F) using an anti-Calbindin antibody of cryosections of aggregates, derived from RAX::GFP knock-in human embryonic stem cells, which were subjected to floating culture up to day 117 from the start of the floating culture in a medium supplemented with BMP4 at 1.5 nM at day 3 from the start of the floating culture.

RAX::GFP knock-in human ES cells (KhES-1-derived; Cell Stem Cell, 2012, 10(6) 771-785) were cultured according to the methods described in "Ueno, M. et al. PNAS 2006, 103(25), 9554-9559" and "Watanabe, K. et al. Nat Biotech 2007, 25, 681-686". As the medium, a medium obtained by adding 20% KSR (KNOCKOUT™ Serum Replacement; Invitrogen), 0.1 mM 2-mercaptoethanol, 2 mM L-glutamine, 1× non-essential amino acid, 5 ng/ml bFGF to DMEM/F12 medium (Sigma) was used. The cultured ES cells were dispersed into single cells by using TrypLE Express (Invitrogen), and the singly dispersed ES cells were suspended in 100 µl of a serum-free medium at $1.2 \times 10^4$ cells per one well of a non-cell adhesive 96 well culture plate (sumilon spheroid plates, SUMITOMO BAKELITE Co., Ltd.) and subjected to floating culture at 37° C., 5% $CO_2$. As the serum-free medium therefor, a serum-free medium obtained by adding 10% KSR, 450 µM 1-monothioglycerol, 1× Chemically defined lipid concentrate, 20 µM Y27632 to a 1:1 mixture of F-12 medium and IMDM medium was used. At day 3 from the start of the floating culture, human recombinant BMP4 (R&D) (final concentration 1.5 nM) was added. A half amount of the culture medium in the well was exchanged every 3 days with the above-mentioned medium not supplemented with a substance acting on the BMP signal transduction pathway. At day 18 from the start of the floating culture, aggregates were transferred from the 96 well plate to a floating culture dish, and floating culture was continuously performed in a medium obtained by adding 10% fetal calf serum, N2 supplement, 100 µM taurine, 500 nM retinoic acid to DMEM-F12 medium. From day 18 from the start of the floating culture, culture was performed under 40% $O_2$. At day 117 from the start of the floating culture, the aggregates were fixed with 4% para-formaldehyde solution, cryosection was prepared, and the tissue structure was confirmed by the immunostaining method. At day 117 from the start of the floating culture, all layers were RAX::GFP positive, and a cell positive to Recoverin, which is a photoreceptor marker, was present (FIG. 5A). In addition, outer layer of the retinal tissue contained a cell positive to Nrl, which is a rod photoreceptor marker (FIG. 5B), and a cell positive to RXR-gamma, which is a cone photoreceptor marker (FIG. 5C), which suggests occurrence of differentiation into rod, cone photoreceptors. Furthermore, a cell positive to Chx10, which is a marker of retinal progenitor cell and bipolar cell (FIG. 5D), a cell positive to Calretinin, which is an amacrine cell marker (FIG. 5 E), and a cell positive to Calbindin, which is a horizontal cell marker (FIG. 5F) were present. The results reveal that the production method of the present invention can produce retinal tissue, which is constituted of various kinds of differentiated retinal layer-specific neural cells, highly efficiently from human ES cells.

Example 6: Production Example of Retinal Layer-Specific Neural Cell

Figure 6:
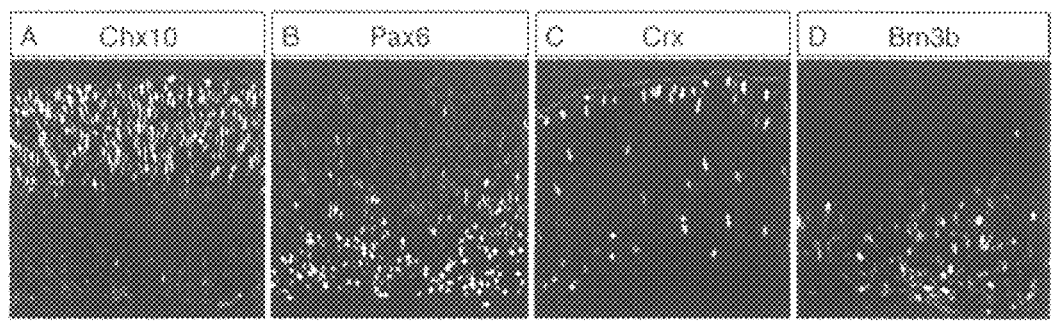
FIG. 6 shows immunostained image (A) using an anti-Chx10 antibody, immunostained image (B) using an anti-Pax6 antibody, immunostained image (C) using an anti-Crx antibody, and immunostained image (D) using an anti-Brn3b antibody of cryosections of aggregates, derived from RAX::GFP knock-in human embryonic stem cells, which were subjected to floating culture up to day 50 from the start of the floating culture in a medium supplemented with BMP4 at 1.5 nM at day 6 from the start of the floating culture.

RAX::GFP knock-in human ES cells (KhES-1-derived; Cell Stem Cell, 2012, 10(6) 771-785) were cultured according to the methods described in "Ueno, M. et al. PNAS 2006, 103(25), 9554-9559" and "Watanabe, K. et al. Nat Biotech 2007, 25, 681-686". As the medium, a medium obtained by adding 20% KSR (KNOCKOUT™ Serum Replacement; Invitrogen), 0.1 mM 2-mercaptoethanol, 2 mM L-glutamine, 1× non-essential amino acid, 8 ng/ml bFGF to DMEM/F12 medium (Sigma) was used. The cultured ES cells were dispersed into single cells by using TrypLE Express (Invitrogen), and the singly dispersed ES cells were suspended in 100 μl of a serum-free medium at $1.2 \times 10^4$ cells per one well of a non-cell adhesive 96 well culture plate (sumilon spheroid plates, SUMITOMO BAKELITE Co., Ltd.) and subjected to floating culture at 37° C., 5% $CO_2$. As the serum-free medium therefor, a serum-free medium obtained by adding 10% KSR, 450 μM 1-monothioglycerol, 1× Chemically defined lipid concentrate, 20 μM Y27632 to a 1:1 mixture of F-12 medium and IMDM medium was used. At day 3 from the start of the floating culture, 50 μl of the serum-free medium was added (total 150 μl). At day 6 from the start of the floating culture, human recombinant BMP4 (R&D) (final concentration 1.5 nM) was added. A half amount of the culture medium in the well was exchanged every 3 days with the above-mentioned medium not supplemented with a substance acting on the BMP signal transduction pathway. At day 18 from the start of the floating culture, aggregates were transferred from the 96 well plate to a floating culture dish, and floating culture was continuously performed in a medium obtained by adding 10% fetal calf serum, N2 supplement, 100 μM taurine, 500 nM retinoic acid to DMEM-F12 medium. From day 18 from the start of the floating culture, culture was performed under 40% $O_2$. At day 50 from the start of the floating culture, the aggregates were fixed with 4% para-formaldehyde solution, cryosection was prepared, and the tissue structure was confirmed by the immunostaining method. At day 50 from the start of the floating culture, all layers were RAX::GFP positive, and a cell positive to Chx10, which is a marker of retinal progenitor cell and bipolar cell (FIG. 6A) and a cell positive to Pax6, which is a marker of ganglion cell and neural cell (FIG. 6B) were present, which suggests formation of multi-layer retinal neural tissues. In addition, a cell positive to Crx, which is a photoreceptor marker (FIG. 6C), and a cell positive to Brn3b, which is a ganglion cell marker (FIG. 6D) were present. The results reveal that the production method of the present invention can produce retinal tissue, which is constituted of various kinds of differentiated retinal layer-specific neural cells, highly efficiently from human ES cells.

Example 7: Production Example of Aggregate Containing Retinal Progenitor Cell, Retinal Tissue and Retinal Layer-Specific Neural Cell, from Induced Pluripotent Stem Cell (iPS Cell)

Human iPS cell line 201B7 (available from RIKEN BioResource center or iPS Academia Japan Inc.) is cultivated according to the methods described in "Ueno, M. et al. PNAS 2006, 103(25), 9554-9559" and "Watanabe, K. et al. Nat Biotech 2007, 25, 681-686". As the medium, a medium obtained by adding 20% KSR (KNOCKOUT™ Serum Replacement; Invitrogen), 0.1 mM 2-mercaptoethanol, 2 mM L-glutamine, 1× non-essential amino acid, 5 ng/ml bFGF to DMEM/F12 medium (Sigma) is used. The cultured iPS cells are dispersed into single cells by using TrypLE Express (Invitrogen), suspended in 100 μl of a serum-free medium at $1.2 \times 10^4$ cells per one well of a non-cell adhesive 96 well culture plate (sumilon spheroid plates, SUMITOMO BAKELITE Co., Ltd.) and subjected to floating culture at 37° C., 5% $CO_2$. As the serum-free medium therefor, a serum-free medium obtained by adding 10% KSR, 450 μl-monothioglycerol, 1× Chemically defined lipid concentrate, 20 μM Y27632 to a 1:1 mixture of F-12 medium and IMDM medium is used. At some time point between day 1 and day 15 from the start of the floating culture, any of human recombinant BMP4 (R&D) (final concentration 1.5 nM), BMP2 (R&D) (final concentration 100 ng/ml), BMP7 (R&D) (final concentration 100 ng/ml), and GDF7 (R&D) (final concentration 100 ng/ml) is added and floating culture is performed. A half amount of the culture medium in the well is exchanged every 3 days with the above-mentioned medium not supplemented with any substance acting on the BMP signal transduction pathway. At day 18 from the start of the floating culture, a part of the aggregates is recovered, fixed with 4% para-formaldehyde, cryosection is prepared, and expression of retinal progenitor cell markers (Rax, Chx10) is confirmed by the immunostaining method. The rest of the aggregates is transferred from a 96 well plate to a floating culture dish, and floating culture is continuously performed in a serum-free medium obtained by adding 10% fetal calf serum, N2 supplement, 100 μM taurine, 500 nM retinoic acid to DMEM-F12 medium. From day 18 from the start of the floating culture, culture is performed under 40% $O_2$. At day 117 from the start of the floating culture, the aggregates are fixed with 4% para-formaldehyde solution, cryosection is prepared, and the tissue structure and expression of a retinal layer-specific neural cell markers (Nrl, RXR-gamma, Recoverin, Chx10, Calretinin, Calbindin) are confirmed by the immunostaining method.

In this way, a retinal progenitor cell, and further, a retinal tissue constituted of various kinds of differentiated retinal layer-specific neural cells can be produced from human iPS cells.

This application is based on a patent application No. 2013-173285 filed in Japan (filing date: Aug. 23, 2013), the contents of which are incorporated in full herein.

INDUSTRIAL APPLICABILITY

According to the production method of the present invention, a retinal progenitor cell, a retinal tissue or a retinal layer-specific neural cell can be produced with high efficiency. In the production method of the present invention, since a retinal progenitor cell, a retinal tissue or a retinal layer-specific neural cell can be obtained by floating culture of an aggregate without adding a basement membrane preparation to a medium, the risk of contamination of the obtained cell or tissue with a component derived from a heterologous species is reduced. The production method of the present invention is highly useful since it efficiently produces a cell group (such as photoreceptor and optic nerve) constituting a retinal tissue, for the purpose of toxicity or drug efficacy evaluation of a chemical substance, etc., a cell treatment and so on, as well as efficiently produces a retinal tissue to be a "tissue material" to be used for tests and treatments for the purpose of application to a toxicity or drug efficacy evaluation using a retinal tissue with a tissue structure, and to a transplantation material for a retinal tissue transplantation treatment.

The invention claimed is:

1. A method for producing a retinal progenitor cell, comprising
   (1) a first step of subjecting pluripotent stem cells to floating culture in a serum-free medium to form an aggregate of pluripotent stem cells, and
   (2) a second step of subjecting the aggregate formed in step (1) to floating culture in a serum-free medium or serum-containing medium each being free of a substance acting on the Sonic hedgehog (Shh) signal transduction pathway that can enhance signal transduction mediated by Shh and containing a substance acting on the bone morphogenic protein (BMP) signal transduction pathway that can enhance signal transduction pathway mediated by BMP at a concentration necessary for differentiation induction into retinal cells from day 1 or later from the start of the floating culture in step (1) until a cell expressing retina and anterior neural fold homeobox (Rax) gene appears, thereby obtaining an aggregate containing retinal progenitor cells.

2. The method according to claim 1, wherein the pluripotent stem cells are primate pluripotent stem cells.

3. The method according to claim 1, wherein the step (1) and step (2) are performed in the presence of a serum replacement.

4. The method according to claim 1, wherein the floating culture is performed in the absence of a basement membrane preparation.

5. The method according to claim 1, wherein the substance acting on the BMP signal transduction pathway is added to the medium between day 1 and day 15 from the start of the floating culture in step (1).

6. The method according to claim 1, wherein the substance acting on the BMP signal transduction pathway that can enhance signal transduction pathway mediated by BMP is BMP4.

7. The method according to claim 6, wherein BMP4 is at a concentration of about 1.5 nM.

8. A method for producing a retinal tissue, comprising
(1) a first step of subjecting pluripotent stem cells to floating culture in a serum-free medium to form an aggregate of pluripotent stem cells,
(2) a second step of subjecting the aggregate formed in step (1) to floating culture in a serum-free medium or serum-containing medium each being free of a substance acting on the Sonic hedgehog (Shh) signal transduction pathway that can enhance signal transduction mediated by Shh and containing a substance acting on the bone morphogenic protein (BMP) signal transduction pathway that can enhance signal transduction pathway mediated by BMP at a concentration necessary for differentiation induction into retinal cells from day 1 or later from the start of the floating culture in step (1) until a cell expressing retina and anterior neural fold homeobox (Rax) gene appears, thereby obtaining an aggregate containing retinal progenitor cells, and
(3) a third step of subjecting the aggregate formed in step (2) to floating culture in a serum-free medium or serum-containing medium each being free of any of a substance acting on the Shh signal transduction pathway that can enhance signal transduction mediated by Shh, a substance acting on the BMP signal transduction pathway that can enhance signal transduction pathway mediated by BMP and a substance acting on the Wingless-related integration site (Wnt) signal pathway that can enhance signal transduction mediated by Wnt, thereby obtaining an aggregate containing retinal tissues and being substantially free of non-neural head ectoderm.

9. The method according to claim 8, wherein the pluripotent stem cells are primate pluripotent stem cells.

10. The method according to claim 8, wherein the pluripotent stem cells are human pluripotent stem cells.

11. The method according to claim 8, wherein the step (1) and step (2) are performed in the presence of a serum replacement.

12. The method according to claim 8, wherein the floating culture is performed in the absence of a basement membrane preparation.

13. The method according to claim 8, wherein the substance acting on the BMP signal transduction pathway that can enhance signal transduction pathway mediated by BMP is one or more proteins selected from the group consisting of BMP2, BMP4, BMP7 and GDF7.

14. The method according to claim 8, wherein the substance acting on the BMP signal transduction pathway that can enhance signal transduction pathway mediated by BMP is added to the medium between day 1 and day 15 from the start of the floating culture in step (1).

15. A method for producing a retinal layer-specific neural cell, comprising
(1) a first step of subjecting pluripotent stem cells to floating culture in a serum-free medium to form an aggregate of pluripotent stem cells,
(2) a second step of subjecting the aggregate formed in step (1) to floating culture in a serum-free medium or serum-containing medium each being free of a substance acting on the Sonic hedgehog (Shh) signal transduction pathway that can enhance signal transduction mediated by Shh and containing a substance acting on the bone morphogenic protein (BMP) signal transduction pathway that can enhance signal transduction pathway mediated by BMP at a concentration necessary for differentiation induction into retinal cells from day 1 or later from the start of the floating culture in step (1) until a cell expressing retina and anterior neural fold homeobox (Rax) gene appears, thereby obtaining an aggregate containing retinal progenitor cells, and
(3) a third step of subjecting the aggregate formed in step (2) to floating culture in a serum-free medium or serum-containing medium each being free of any of a substance acting on the Shh signal transduction pathway that can enhance signal transduction mediated by Shh, a substance acting on the BMP signal transduction pathway that can enhance signal transduction pathway mediated by BMP and a substance acting on the Wingless-related integration site (Wnt) signal pathway that can enhance signal transduction mediated by Wnt until the intended retinal layer-specific neural cells appear, thereby obtaining an aggregate containing retinal tissues containing the intended retinal layer-specific neural cells and being substantially free of non-neural head ectoderm.

* * * * *